(12) United States Patent
Logan et al.

(10) Patent No.: US 7,058,444 B2
(45) Date of Patent: Jun. 6, 2006

(54) COMPUTER METHOD AND SYSTEM FOR READING AND ANALYZING ECG SIGNALS

(75) Inventors: Beth T. Logan, Cambridge, MA (US); Pedro J. Moreno, Cambridge, MA (US); David Goddeau, Watertown, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 100 days.

(21) Appl. No.: 10/818,007

(22) Filed: Apr. 5, 2004

(65) Prior Publication Data

US 2005/0222507 A1    Oct. 6, 2005

(51) Int. Cl.
A61B 5/04 (2006.01)

(52) U.S. Cl. ...................... 600/523; 600/515

(58) Field of Classification Search ............... 600/509, 600/515–519, 523; 128/920, 922
See application file for complete search history.

(56) References Cited

U.S. PATENT DOCUMENTS

| | | | |
|---|---|---|---|
| 4,340,065 A | 7/1982 | Gessman | |
| 5,086,778 A | 2/1992 | Mueller et al. | |
| 5,090,418 A | 2/1992 | Squires et al. | |
| 5,730,142 A | 3/1998 | Sun et al. | |
| 6,308,094 B1* | 10/2001 | Shusterman et al. | 600/516 |
| 6,463,320 B1 | 10/2002 | Xue et al. | |
| 6,564,090 B1 | 5/2003 | Taha et al. | |
| 2001/0020136 A1 | 9/2001 | Sweeney | |
| 2002/0143263 A1 | 10/2002 | Shusterman | |
| 2003/0149678 A1 | 8/2003 | Cook | |
| 2003/0176802 A1* | 9/2003 | Galen et al. | 600/523 |
| 2004/0243328 A1* | 12/2004 | Rapp et al. | 702/71 |
| 2005/0004485 A1* | 1/2005 | Crosby et al. | 600/513 |
| 2005/0177049 A1* | 8/2005 | Hardahl et al. | 600/509 |

FOREIGN PATENT DOCUMENTS

WO    WO 03/077754    9/2003

* cited by examiner

Primary Examiner—Robert E. Pezzuto
Assistant Examiner—Jessica L. Reidel
(74) Attorney, Agent, or Firm—Richard P. Lange

(57) ABSTRACT

Computer method and apparatus for reading and analyzing ECG signals includes applying a plurality of heart condition detectors to a subject ECG signal. Each detector produces a respective indication of likelihood of certain heart conditions existing in the subject. A lattice having annotations of the different detector heart conditions is formed from the detector indications. The lattice enables medical personnel to navigate through and hence more easily read the ECG signal data. The lattice effectively provides an indexed or annotated version of the subject ECG signal.

20 Claims, 5 Drawing Sheets

US 7,058,444 B2

COMPUTER METHOD AND SYSTEM FOR READING AND ANALYZING ECG SIGNALS

BACKGROUND OF THE INVENTION

The electrocardiogram (ECG or sometimes EKG) is a valuable diagnostic tool used extensively by cardiologists worldwide. The ECG records the electrical activity of the heart detected through small electrodes (leads) placed on the patient's chest, wrists and ankles. An examination in a doctor's office might typically collect readings from twelve electrodes and would normally last only up to half an hour. An alternative is for doctors to issue to patients a monitoring device that they take home and wear for a day or two. In this case, typically data from only one or two leads is collected.

The data from the ECG leads is normally recorded on paper or stored in the monitoring device's memory. In the case of the examination in the doctor's office, a physician or nurse scans the printouts by hand since there is relatively little data. For the home monitoring case, again scanning is mostly performed by hand. This may be feasible for 24 hours worth of data. However, many heart conditions are transient and infrequent, occurring only once a week or even less often. For these cases, days or weeks of monitoring may be required, generating a large amount of data that must be scanned, either by machine or by a trained professional, in order to reveal abnormal conditions.

Thus, most modern ECG machines still rely on a doctor or technician printing out the signal readings and looking through it by hand. This is not only time consuming but could result in important symptoms being overlooked. Furthermore, some ECG machines provide limited analysis of the signal, e.g., heart rate, fibrillation detection and the like.

SUMMARY OF THE INVENTION

Doctors typically want or need to only look at "interesting" sections of the ECG signals. The present invention alleviates the need for a professional to scan all of the data by hand, allowing fast navigation through the ECG signal. Further, the present invention makes very long term ECG data collection and review feasible in contrast to current techniques in which it is impractical to scan by hand all of the generated data. In turn, this enables detection of heart conditions with very infrequent symptoms but which are nonetheless serious.

In one embodiment, the present invention method of reading and analyzing ECG signals includes the computer implemented steps of:

(a) receiving a subject ECG signal of a subject;

(b) applying a plurality of heart condition detectors to the subject ECG signal and therefrom producing indications of the likelihood of certain heart conditions existing in the subject; and (c) forming a lattice having annotations from the produced indications, the lattice enabling one to navigate through the subject ECG signal.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention alleviates the need for a professional to scan all of the data by hand, allowing fast navigation through a subject ECG signal. By way of overview, the present invention converts the subject ECG signal from voltages over time to an alphabet of symbols. Each symbol corresponds to a known heart pattern. In order to automatically convert the ECG signal to a symbolic representation, the many algorithms published in the ECG literature are used. For example, to detect myocardial ischemia, a condition in which heart muscles do not receive enough oxygen, the algorithm in "Automatic Detection of ST-T Complex Changes on the ECG Using Filtered RMS Difference Series: Application to Ambulatory Ischemia Monitoring," J. Garcia, S. Olmos and P. Laguna, IEEE Transactions on Biomedical Engineering, Vol. 47, No. 9, September 2000, can be applied to the ECG signal.

In the present invention, detectors are implemented for as many heart conditions as desired. Currently, over 80 syndromes can be detected from ECG's by cardiologists (see "ABC of Clinical Electrocardiography" by Francis Morrus, BMJ Publishing Group, 01-2003, ISBN 0727915363 and "ECGs by Example", by Jenkings and Gerred, 1997, IBSN 0443056978). For a number of these conditions, algorithms (detectors) have been published which automatically analyze the ECG and return either a binary "yes/no" decision as to whether the condition is present at time t or a confidence score describing how confident the algorithm is of detecting that signal.

The aim of the present invention is not to detect abnormal heart conditions but to facilitate professionals' discovery of them in vast quantities of data. To this end, the present invention constructs a lattice over the ECG signal and uses the lattice to aid navigation through the data. A lattice is a directed graph (left to right) showing many possible alternative paths through the maze of hypotheses. The lattice consists of nodes, which correspond to points in time, and arcs, which correspond to transitions between nodes.

Figure 1:
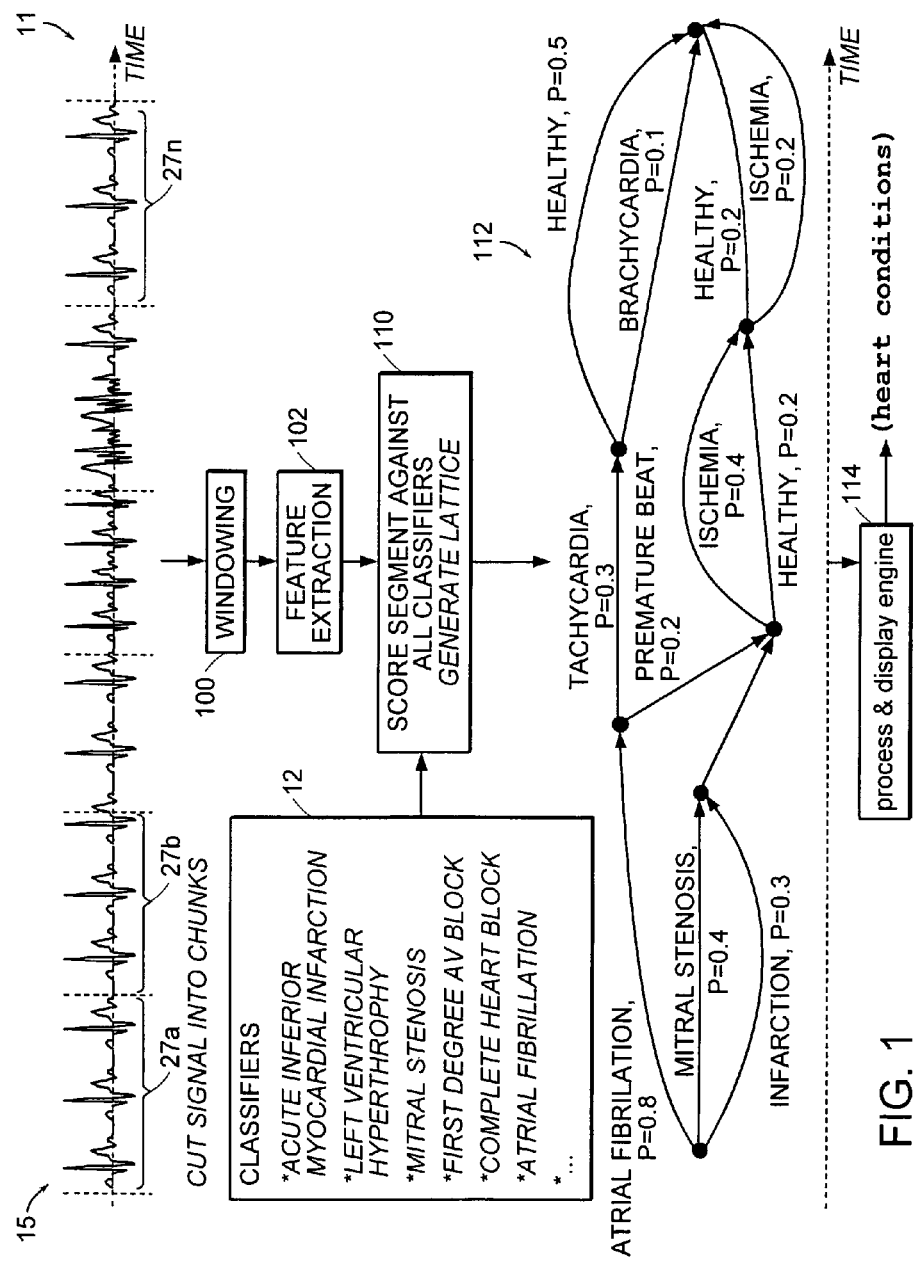
FIGS. 1 and 4 are schematic diagrams of the present invention lattice construction and analysis.

The invention process 11 of constructing a lattice from an ECG signal is shown in FIG. 1. The steps are as follows. First, the subject ECG signal 15 is segmented into chunks 27 (data segments) by windowing step 100. The length of each chunk 27 is arbitrary but should be sufficiently long such that the detection algorithms can make a decision for that chunk. Feature extraction step 102 assists in determining boundaries of chunks 27 (i.e., chunk length). Example techniques for feature extraction include: detecting change in signal pattern, detecting change in overall signal amplitude and detecting change in frequency of 0-line crossings. See "ABC of Clinical Electro Cardiography" by Francis Morrus cited above. Chunks 27 can also potentially overlap in time. A typical chunk length might be fifteen minutes worth of data.

The various heart condition detectors 12 (mentioned previously) or other classifiers are then applied to each chunk at step (scoring module) 110. Preferably each classifier/detector 12 is directed at detecting a respective specific heart condition given an input ECG signal. Each classifier/detector 12 on output provides a number (for example, simply 1 or 0) or score describing the likelihood of that particular heart condition being present in the chunk 27. Each detector 12 may also generate a confidence level or error rate of its score result. Using the numerical results (scores) of the detectors 12, an N×M lattice 112 is constructed where N is the number of chunks 27 and M is the number of heart conditions in the alphabet. The alphabet may include the "normal" condition. If more than one detector 12 is implemented for the same heart condition, these can be either included separately in the lattice 112 or their scores combined using voting or another combination technique.

It may be necessary to normalize or weight the scores from the different classifiers 12 so they can be compared to each other. The weighting may be empirical or it can reflect prior beliefs about those conditions in the general population or specific to the patient according to his/her medical history.

In a preferred embodiment, the lattice 112 initially contains one node per sample (chunk 27) of the subject ECG signal 15 or sequence to be represented. The node is labeled by time (or sequence order). In practice, many nodes can be removed as uninteresting without loss of information. Initial time arcs are created linking each node to its successor in time. The arcs can be explicitly represented or can remain implicit.

Additional arcs are created by scoring multiple classifiers or feature detectors 12 against the subject ECG signal 15. These classifiers can be run in series or in parallel. Each classifier 12 decides when a segment 27 of the subject signal 15 matches its internal model. When this happens, an arc is created, spanning the matched segment 27, and labeled with the class or feature (e.g., "atrial fibrillation", "infarction", "ischemia", etc.) that was detected. The label may also indicate level of confidence (P=0.x) of the feature detected as illustrated in FIG. 1. As such, the labels serve as helpful annotations for the medical professional.

Each path through the lattice 112 corresponds to an alternative segmentation of the ECG signal 15. A time axis or other indication of time enables correspondence between the lattice 112 and the original ECG signal 15.

Figure 4:
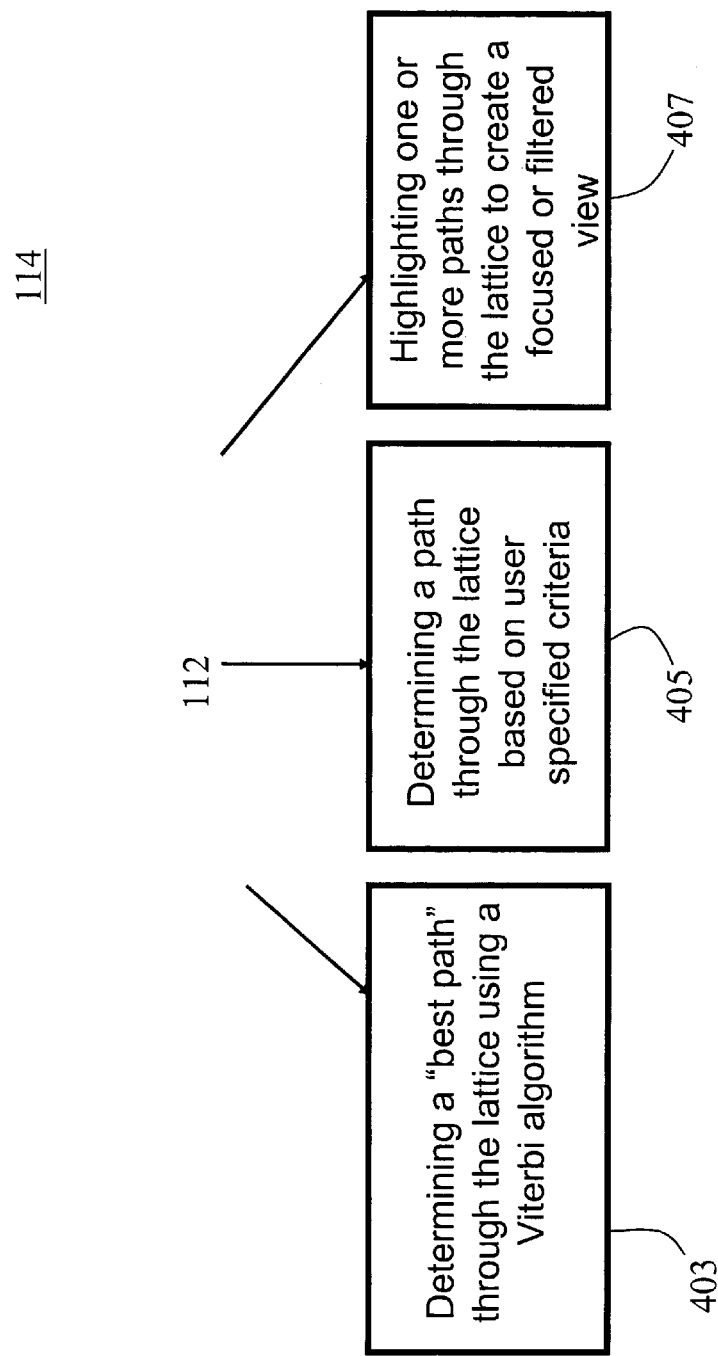

Next, the generated lattice 112 is processed by process and display engine 114 in a variety of ways 403, 405, 407 (FIG. 4) to aid ECG analysis. First, a "best path" through the lattice 112 is determined using the Viterbi algorithm (step 403). This produces the most likely heart condition, including normal, for each chunk 27. Such could be used, for example, by a physician to show all chunks (segments of subject ECG signal 15) which probably exhibit Condition A. For infrequently occurring conditions, this would allow a professional to quickly "zoom" to (filter and focus on) the sections of the ECG readout 15 which exhibit a particular condition.

The output of a Viterbi search over the lattice 112 can also be used to visualize the ECG signal 15. Here, a different color is assigned to each heart condition in the alphabet and a timeline is displayed with each chunk 27 shown in the color of the more likely condition. Again, this allows the professional to zoom to (quickly see/view at a glance) areas showing abnormal heartbeats (step 407).

The lattice 112 may be processed in yet more ways (step 405). For example, digging deeper than simply the best path, the physician can ask a variety of quite complex queries. For example, he could ask to view all the chunks 27 with likelihood (confidence P value) of Condition A greater than x and that of Condition B greater than y. Or to view chunks for which Condition C has likelihood (P value) greater than z for n seconds.

Another type of possible search is for a sequence of events. For example, the physician could search for Condition A, followed by Conditions B and C. This is a standard type of search through a lattice 112. It can be performed either by scanning through the lattice for a particular pattern or if it is known that for example three-condition sequences are commonly searched for, then an index of all possible three-condition sequences can be built and utilized.

The full lattice 112 may also be used to construct another type of useful visualization of the data. Here, the full grid is displayed as a 2-D plot with the color of each point reflecting whether the number is large or small. For example, large numbers can be assigned red, small numbers blue and intermediate numbers are assigned colors between red and blue in the spectrum (or vice versa). The display is similar to a checkerboard pattern with red and orange sections indicating that a particular condition is present or likely to be present. A physician can again use this visualization to zoom to (focus his attention to) abnormal sections of the initial ECG signals 15.

In yet another embodiment, the invention system 11 is used to study correlations between ECG's 15 collected from more than one patient. Either the Viterbi best path or the full lattice 112 can be used.

To accomplish the foregoing, process and display engine 114 employs known techniques for selecting paths based on user specified criteria 405 and for sorting, color coding, highlighting display of, filtering, zooming, etc. paths in part or whole 407.

Figure 2:
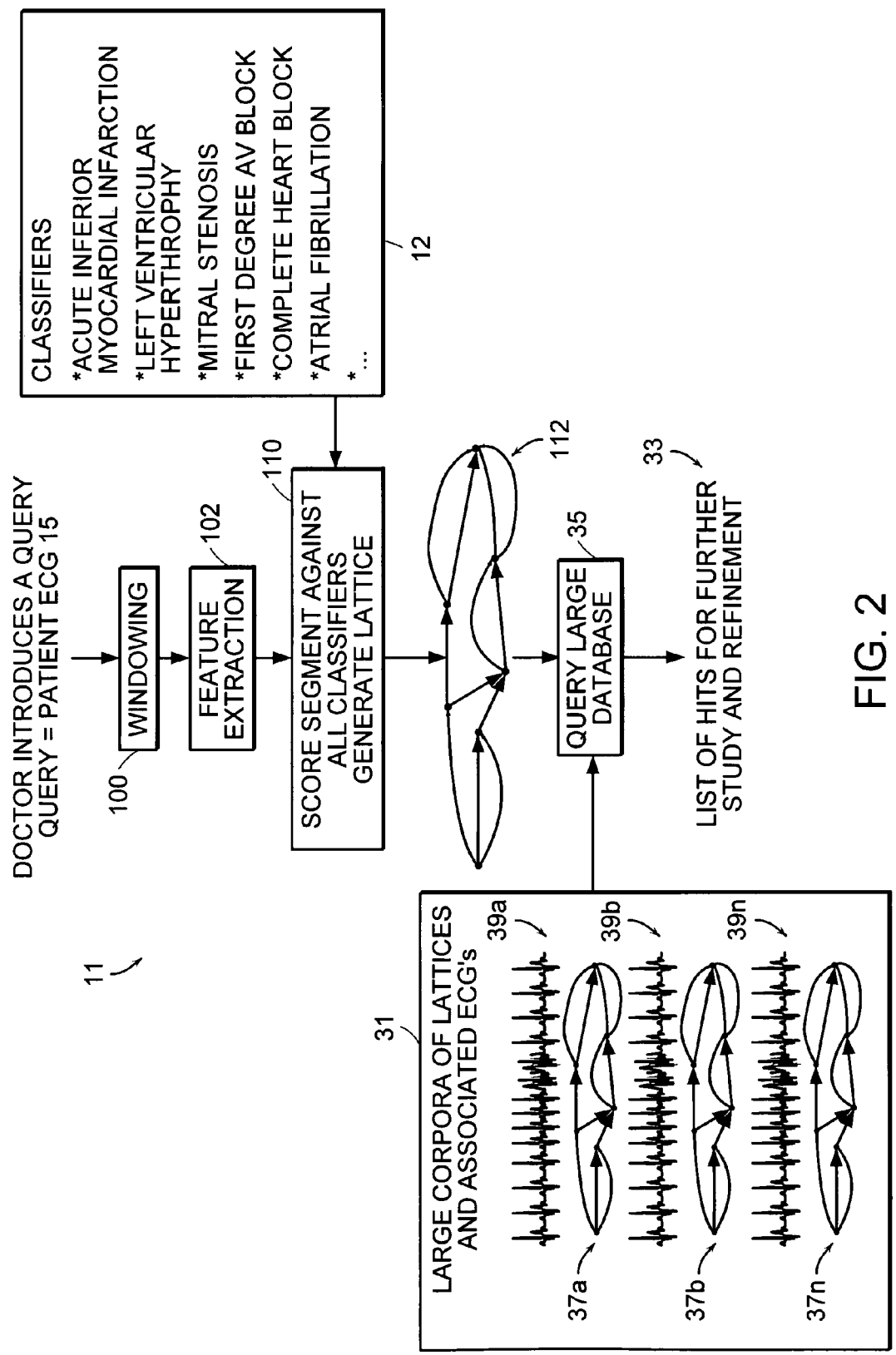
FIG. 2 is a schematic diagram of querying by example that applies the lattice construction of FIG. 1.

Also, if a doctor has an ECG recording 15 that he cannot identify, he may search for this in the lattices of pre-recorded records. An example of this is shown in FIG. 2. Here the query lattice 112 (formed by the process 11 of FIG. 1 from a patient's ECG 15) is compared with a data store 31 of lattices and the closest matches 33 are returned. These matches may be further filtered by patient age, medical history, weight and the like. The closest match gives an initial or preliminary diagnosis for the subject patient's ECG 15.

The data store 31 may be implemented as a database holding previously generated lattices 37 and corresponding ECG's 39 that produced those lattices of various patients. The query engine 35 of the database management system then uses the current patient's (subject) lattice 112 (the "query" lattice) as input. The query engine 35 determines the predefined lattices 37 that most closely match the input subject lattice 112. The heart conditions associated with the closest matching predefined lattices 37 provide an analysis of the subject ECG 15.

Further, instead of generating a lattice 112, each ECG signal 15 may be converted to a "signature" vector. Each component of the vector is the sum or another combination of the classifier 12 outputs for each chunk 27. Thus time information is thrown away but the ECG signal 15 is represented in a simple form (the signature vector). This would not allow zooming to important parts of the original ECG signal 15 but would however facilitate fast comparison between patient ECG's and would speed diagnosis.

Also, some patients with a history of heart conditions may have permanently abnormal ECG's (due to permanent tissue damage). For these patients, it may be desirable to discover only those portions of the ECG signal 15 which are significantly different from the usual abnormal state. In this case, invention apparatus 11 allows the professionals either to modify the thresholds and settings of the classifiers 12 or to completely ignore the output from some classifiers 12.

Finally, although this disclosure has been written with indexing/visualization aims in mind, it is clear that a program which analyzes the lattice 112 in real time could be used to raise alarms of various syndromes.

Figure 3A:
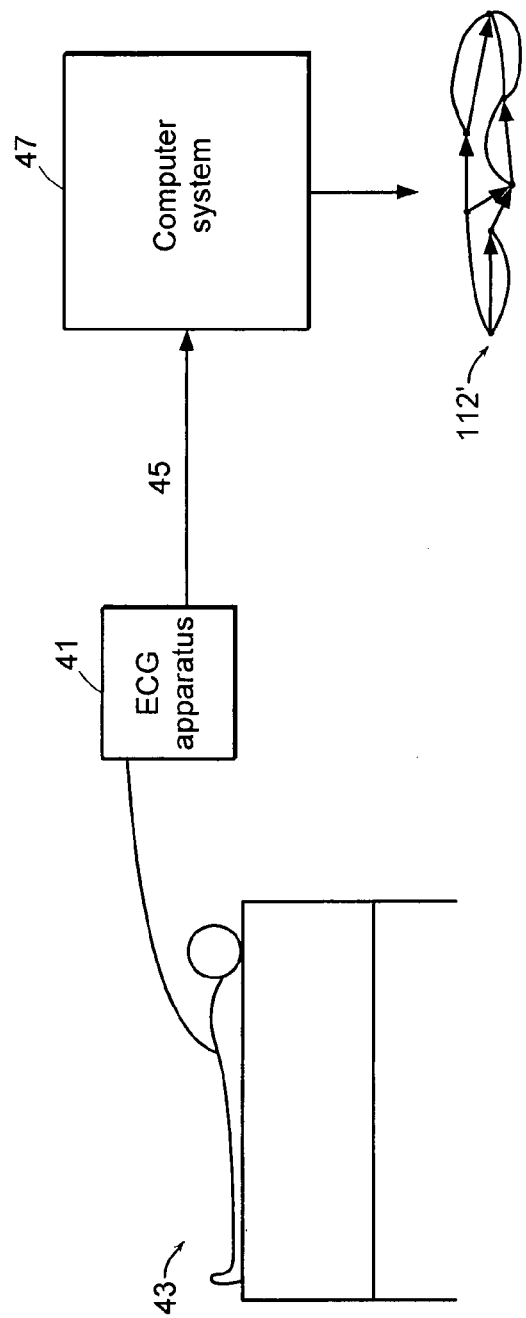
FIGS. 3a and 3b are schematic and block diagrams of a computer system employing the present invention.
Figure 3B:
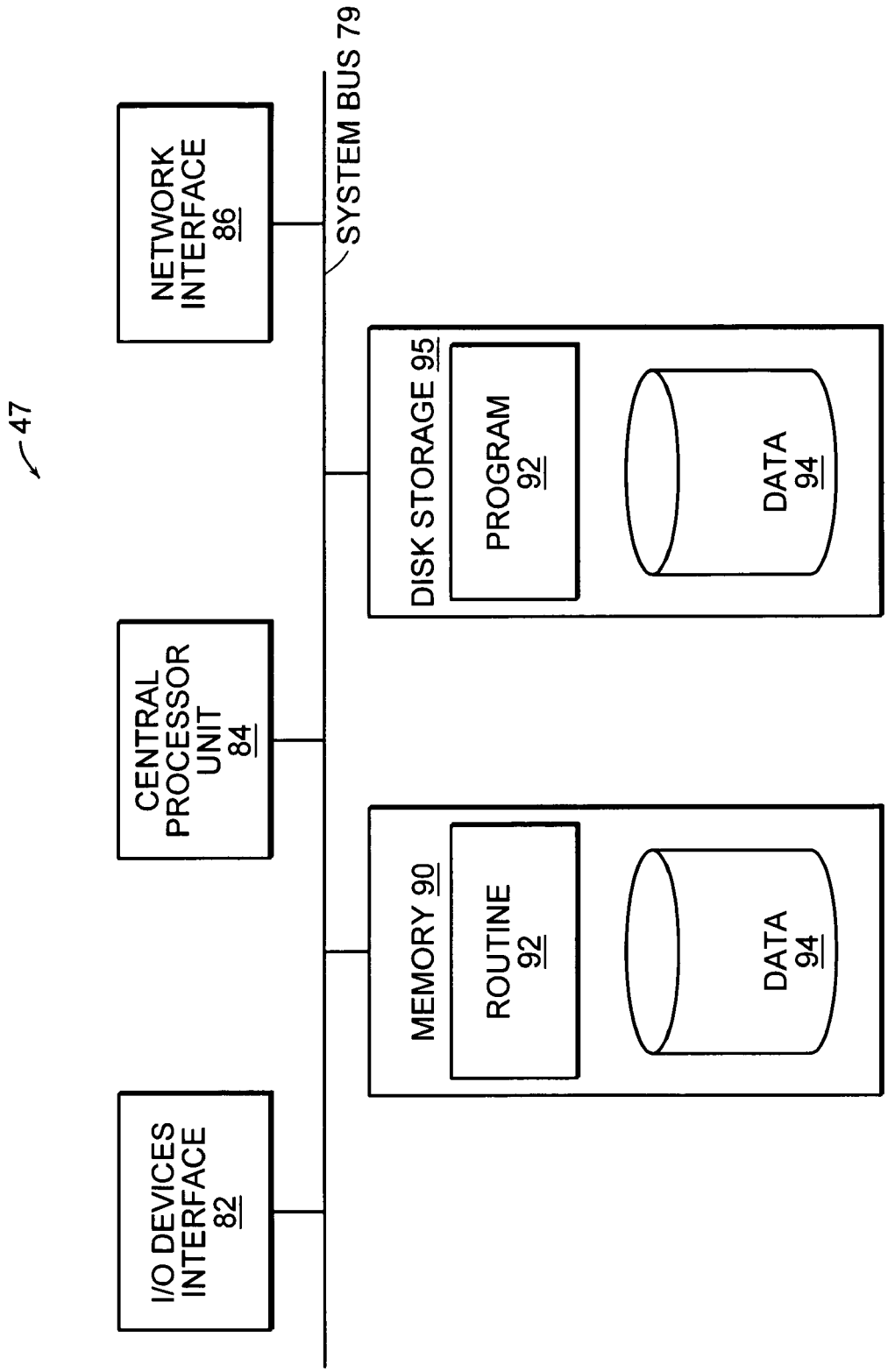

Illustrated in FIGS. 3a and 3b is a computer system embodying the present invention. ECG apparatus 41 is connected to a patient (subject) 43. Readings (signals) 45 from the ECG apparatus 41 are input (e.g., downloaded or otherwise transmitted) to computer system 47 implementing the present invention. In particular, computer system 47 (i) constructs a lattice 112' (including labels, annotations, etc.) corresponding to subject ECG signals 45 and (ii) provides display processing and querying of the lattice 112' to assist the physician in navigating through and more pointedly (in a focused and/or filtered manner) visualizing the ECG data as described above in FIGS. 1 and 2. As such, computer system 47 serves as a tool for assisting with the reading and analysis of ECG signals/data.

As shown in FIG. 3b, each computer system 47 preferably contains system bus 79, where a bus is a set of hardware lines used for data transfer among the components of a computer. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., displays, printers, speakers, etc.) to the computer system. Subject ECG signals 45 are received through I/O device interface 82. Network interface 86 allows the computer system to connect to various other devices attached to a network. Memory 90 provides volatile storage for computer software instructions (e.g., Program Routines 92 and Data 94) used to implement an embodiment of the present invention. Program routines 92 include invention process 11, heart detector/classifiers 12 and query engine 35 and database subsystem for example of FIGS. 1 and 2. Data 94 includes the corpora 31 of stored lattices 37 and associated ECG signals 39. Disk storage 95 provides non-volatile storage for computer software instructions and data used to implement an embodiment of the present invention. Central processor unit 84 is also attached to system bus 79 and provides for the execution of computer instructions.

Network interface 86 enables invention program (routine) 11 to be downloaded or uploaded across a network (e.g., local area network, wide area network or global network). I/O device interface 82 enables invention process 11 to be ported between computers on diskette or other computer readable medium (CD-ROM, etc.). Other transmission of process 11 in whole or in part between computers is in the purview of one skilled in the art. Accordingly, invention process 11 may be run on a standalone computer, distributed across computer networks, or executed in a client-server fashion or other arrangement.

While this invention has been particularly shown and described with references to preferred embodiments thereof, it will be understood by those skilled in the art that various changes in form and details may be made therein without departing from the scope of the invention encompassed by the appended claims.

For example, the invention system may be applied to human or other subjects. Also, restated, the present invention provides a method and system for indexing or annotating ECG signals (readings). The labels of the generated lattice 112 provide indications of heart conditions and levels of confidence of detected conditions. The ECG signal together (either overlaid or otherwise correlated) with these labels (the lattice 112) provide the physician-user with an indexed or annotated version of the ECG.

What is claimed is:

1. A method of reading and analyzing ECG signals comprising the computer implemented steps of:
    receiving a subject ECG signal of a subject; applying a plurality of heart condition detectors to the subject ECG signal and therefrom producing indications of likelihood of certain heart conditions existing in the subject; and
    forming a lattice having annotations from the produced indications, the lattice enabling one to navigate through the subject ECG signal.

2. A method as claimed in claim 1 further comprising the step of traversing the lattice in a manner that shows most likely heart conditions detected in the subject ECG signal.

3. A method as claimed in claim 2 wherein the step of traversing employs a Viterbi algorithm.

4. A method as claimed in claim 1 further comprising the step of determining a path through the lattice based on user-specified criteria.

5. A method as claimed in claim 4 wherein the user-specified criteria includes any combination of type of heart condition, likelihood threshold of a certain heart condition, time length of ECG signal indicating a certain heart condition, sequence of heart conditions and similarity between ECG signals indicating heart conditions.

6. A method as claimed in claim 1 further comprising:
    providing a database of predetermined lattices having respective associated heart conditions; and
    comparing the formed lattice against those in the database to determine heart conditions of the subject.

7. A method as claimed in claim 1 further comprising the step of highlighting one or more paths through the lattice such that a focused and/or filtered view of the subject ECG symbol to the user is enabled.

8. Computer apparatus for reading and analyzing ECG symbols comprising:
    an input member for receiving a subject ECG signal of a subject;
    a plurality of heart condition detectors; and
    a scoring module coupled to receive the subject ECG signal from the input member and for applying each detector to the subject ECG signal and therefrom producing indications of likelihood of certain heart conditions existing in the subject, wherein the scoring module forms a lattice from the produced indicators, the lattice enabling one to navigate through the subject ECG signal.

9. Computer apparatus as claimed in claim 8 wherein the formed lattice provides an indexed or annotated view of the subject ECG signal.

10. Computer apparatus as claimed in claim 8 further comprising a process and display engine that enables traversing of the lattice in a manner that shows most likely heart conditions detected in the subject ECG signal.

11. Computer apparatus as claimed in claim 10 wherein the process and display engine employs a Viterbi algorithm to traverse the lattice.

12. Computer apparatus as claimed in claim 8 further comprising a process and display engine that determines a path through the lattice based on user-specified criteria.

13. Computer apparatus as claimed in claim 12 wherein the user-specified criteria includes any combination of type of heart condition, likelihood threshold of a certain heart condition, time length of ECG signal indicating a certain heart condition, sequence of heart conditions and similarity between ECG signals indicating heart conditions.

14. Computer apparatus as claimed in claim 8 further comprising:

a database storing predefined lattices having respective determined heart conditions; and a query engine for comparing the formed lattice against the predefined lattices stored in the database to determine heart conditions of the subject.

15. Computer apparatus as claimed in claim 8 further comprising a process and display engine that highlights one or more paths through the lattice such that a focused and/or filtered view of the subject ECG signal to the user is enabled.

16. A computer system for reading and analyzing ECG signals comprising:

means for applying a plurality of heart condition detectors to a subject ECG signal of a subject and therefrom producing indications of likelihood of certain heart conditions existing in the subject; and lattice means forming a lattice having annotations from the produced indications, the lattice enabling one to navigate through the subject ECG signal.

17. A computer system as claimed in claim 16 wherein the lattice means includes means for traversing the lattice in a manner that shows most likely heart conditions detected in the subject ECG signal.

18. A computer system as claimed in claim 16 further comprising means for determining a path through the lattice based on user-specified criteria.

19. A computer system as claimed in claim 18 wherein the user-specified criteria includes any combination of type of heart condition, likelihood threshold of a certain heart condition, time length of ECG signal indicating a certain heart condition, sequence of heart conditions and similarity between ECG signals indicating heart conditions.

20. A computer system as claimed in claim 16 further comprising means for highlighting one or more paths through the lattice.

\* \* \* \* \*